United States Patent [19]

Hoffer

[11] E Patent Number: Re. 31,626

[45] Reissued Date of Patent: Jul. 10, 1984

[54] INTRAOCULAR LENS

[76] Inventor: Kenneth J. Hoffer, 2001 Santa Monica Blvd., Ste. 460W, Santa Monica, Calif. 90404

[21] Appl. No.: 389,708

[22] Filed: Jun. 18, 1982

Related U.S. Patent Documents

Reissue of:

[64] Patent No.: 4,244,060
Issued: Jan. 13, 1981
Appl. No.: 965,324
Filed: Dec. 1, 1978

[51] Int. Cl.[3] ..... A61F 1/16; A61F 1/24

[52] U.S. Cl. ..... 3/13

[58] Field of Search ..... 3/13, 1

[56] References Cited

U.S. PATENT DOCUMENTS

| | | | |
|---|---|---|---|
| 3,866,249 | 2/1975 | Flom | 3/13 |
| 4,014,049 | 3/1977 | Richards et al. | 3/13 |
| 4,041,552 | 8/1977 | Ganias | 3/13 |
| 4,073,014 | 2/1978 | Poler | 3/13 |
| 4,073,015 | 2/1978 | Peyman et al. | 3/13 |
| 4,110,848 | 9/1978 | Jensen | 3/13 |
| 4,159,546 | 7/1979 | Shearing | 3/13 |

OTHER PUBLICATIONS

"The Lens", (Advertisement), Shearing Posterior Chamber Lens Model 101.

*Primary Examiner*—Ronald L. Frinks
*Attorney, Agent, or Firm*—Spensley, Horn, Jubas & Lubitz

[57] ABSTRACT

An intraocular lens includes a body lens and a plurality of lens-centering filaments extending outwardly in a common plane from spaced rim portions of the lens body. The lens is particularly adapted for implantation in the eye posterior chamber after extracapsular cataract extraction. When the filament ends are inserted into the cleft of the capsule, the resilience of the filaments centers the lens behind the pupil. An annular lip having at least one opening projects from the rear face of the lens body and seats against the posterior capsule. A discission can be easily performed without dislodging the lens by inserting the discission instrument through the opening in the lip and into the space behind the lens. The lip also limits the progress of vitreous humor toward the anterior chamber after a discission, and may limit lens fiber growth on the posterior capsule within the lip region. In an optional embodiment, fluid flow channels are provided through the lens to prevent pupillary block.

17 Claims, 7 Drawing Figures

INTRAOCULAR LENS

Matter enclosed in heavy brackets [ ] appears in the original patent but forms no part of this reissue specification; matter printed in italics indicates the additions made by reissue.

BACKGROUND OF THE INVENTION

1. Field of the Invention

The present invention relates to an intraocular lens, and particularly to a self-centering, posterior chamber lens adapted for mounting in the capsule following extracapsular cataract extraction.

2. Description of the Prior Art

In the human eye, the lens is situated behind the pupil and iris, and functions to focus light entrant through the cornea and pupil onto the retina at the rear of the eye. The lens is a biconvex, highly transparent structure made of slender, curved rod-shaped ectodermal cells in concentric lamellae surrounded by a thin capsule. The lens capsule is supported at its periphery by suspensory ligaments, called zonules, that are continuous with the ciliary muscle. Contraction of this muscle relaxes the zonules, allowing the lens to become more spherical, thereby altering its focal length.

A cataract condition results when the material within the lens capsule becomes clouded, thereby obstructing the passage of light. To correct this condition, two forms of surgery are used. In intracapsular cataract extraction, the entire lens is removed intact. To accomplish this, the surgeon severs the zonules or suspensory ligaments about the entire periphery of the capsule, and removes the entire lens with the capsule and its content material intact.

In extracapsular cataract extraction, an incision is made through the front wall (the "anterior capsule") of the lens, and the clouded cellular material within the capsule is removed through this opening. Various scraping, suction or phacoemulsification techniques are used to accomplish such extraction. The transparent rear capsule wall (the "posterior capsule") remains in place in the eye. Also remaining in place are the zonules, and peripheral portions of the anterior capsule (the "anterior capsule flaps").

Both intracapsular and extracapsular extraction eliminate the light blockage due to the cataract. However, the light now entrant through the cornea and pupil is totally unfocused since there is no longer a lens in the eye. Appropriate focusing can be achived by a lens (i.e., a contact lens) exterior to the eye. This approach, though generally satisfactory, has the disadvantage that when the external lens is removed (i.e., when the contact lens is "taken out"), the patient effectively has no sight. A preferred alternative is to implant an artificial lens directly within the eye. One objective of the present invention is to provide such an intraocular lens.

Although at present more intracapsular lens removals are performed than extracapsular extractions, there are certain undesirable complications which may result from intracapsular surgery. The first involves "vitreous loss." The entire region of the eye behind the lens normally is filled with a jelly-like material called the vitreous humor. When the lens is removed intact, the vitreous humor comes up through the pupil and may escape from the eye through the incision that was made to accomplish the intracapsular extraction. Adverse side effects can occur.

Another complication of intracapsular surgery is called cystoid macula edema (CME). This is an edema or swelling of the macula of the retina. This may be due to certain enzymes which are released from the iris and migrate through the vitreous humor back to the macula, causing swelling. This is a serious complication. The incidence of both vitreous loss and CME is substantially reduced in the case of extracapsular extraction, since the posterior capsule remains in place and prevents the vitreous humor from reaching the anterior chamber. Thus from the viewpoint of reducing post-surgical complications, extracapsular extraction is preferred, and it is a further object of the present invention to provide an intraocular lens the use of which is particularly advantageous with extracapsular extractions.

Various forms of intraocular lenses are known. Generally these fall into two major classes, the anterior chamber lenses which are situated forward of, or mounted to the iris, and posterior chamber lenses which are situated behind the iris and may be mounted within the cleft or fornix of the capsule which remains in place after extracapsular surgery. The present invention is of the latter type.

Historically, the earliest posterior chamber lens implants were performed by Harold Ridley in the early 1950's. The Ridley biconvex lens was about the same shape, but had approximately 1 mm smaller diameter than the normal human lens. Its weight in air was 112 mg, an extremely heavy weight for an object to be implanted in the eye. The weight and relatively large diameter caused the Ridley lens to exert undue pressure on the ciliary body, the annular structure on the inner surface of the eye surrounding the lens and including the ciliary muscle and the ciliary process to which the zonules are connected. Other adverse side effects occurred. Glaucoma was noted. In come instances, the lens became loose and fell into the back of the eye. Many cases of downward decentration were noted, wherein the lens shifted downwardly so that its axis was no longer centered with respect to the pupil. For all of these reasons, the Ridley lens soon was abandoned.

A related lens designed by Strampelli for use in the anterior chamber also was tried in the early 1950's. This lens seated in the "angle" of the eye, where the cornea and iris are joined. Often, the use of such lens caused destruction of the endothelium, a very thin layer of live cells on the interior of the cornea. This is a very serious complication, and use of this form of angle-fixated anterior chamber lens soon was stopped.

Next came a series of anterior chamber lenses which were mounted to the iris. Amongst the earliest is the so-called Copeland or Epstein iris plane lens. This is a one-piece, cross-shaped structure having a generally plano-convex central lens and four planar blades projecting respectively from the top, bottom and sides of the lens. The lens is mounted in the pupil by inserting two diagonally opposite blades (usually the ones at top and bottom) behind the iris, and allowing the two remaining blades to seat against the front of the iris. Thus the structure actually is fixed directly to the iris. This eliminates the centration problem, since the lens itself is situated in the pupil, and also eliminates the problems associated with lenses that seat against the ciliary sulcus or against the angle. However, dilation of the pupil is difficult with this lens.

Another iris fixated lens was developed by C. D. Binkhorst, and is known as the "iris clip lens" or the Binkhorst four-loop lens. This lens includes a pair of anterior loops projecting from the top and bottom of the lens which seat against the front of the iris. A second pair of loops extend from the rear of the lens and are formed in an L-shape when viewed from the side. These posterior loops clip behind the iris. The Binkhorst iris clip lens is relatively easy to implant, and has the advantage of being very light. Typically, it weighs about 3 mg in aqueous. However, it has the disadvantage that when the pupil is dilated, the lens may fall out of place. In that instance, it could float forward against the cornea, destroying the endothelim or, in the case of an intracapsular extraction, it could fall into the back of the eye damaging the retina.

This dislocation problem was solved by Jan G. F. Worst with his "iris medallion lens." This iris fixated lens also uses a pair of posterior loops, L-shaped when viewed from the side, which clip behind the iris. The optical portion of the lens is centered in the pupil. A haptic rim surrounds the optical portion and overlies the front of the iris. The haptic rim is of non-uniform width, and has two holes in its widest region. The surgeon uses these holes to suture the lens directly to the iris. This locks the lens in place, and eliminates some of the problem of lens dislocation. The Worst iris medallion lens is the most widely accepted form of intraocular lens. It is estimated that over twenty thousand such lenses have been implanted in humans in the United States alone.

Although the suturing of the iris medallion lens solved the dislocation problem, the use of sutures is itself advantageous. Sutures are subject to biodegradation and/or displacement and are surgically difficult to implement. It is an object of the present invention to provide a lens the placement, fixation and centration of which is accomplished without suturing.

Other attempts have been made to accomplish this objective. The Choyce Mark VIII anterior chamber lens is a thin, generally flat unitary structure having the appearance, when viewed frontally, of an elongated rectangle having rounded corners and notched ends. The rounded corners seat in the angle, and center the plano-convex or biconvex optical portion in front of the pupil. The lens is easy to implant, and thus has gained acceptance by many surgeons. However, cases of CME have been noted with these lenses. Also, tension is placed on the angle, resulting in tenderness to the eye, particularly when rubbed.

Another form of self-centering lens was developed by Barraquer, initially for anterior chamber use and later adapted for placement in the posterior chamber. This lens includes a pair of hook-shaped flexible loops coming off of opposite sides of the optical portion. Since one end of each loop is free, the loops would flex sufficiently to snap in place. When installed in the anterior chamber, the hooks seated in the angle.

Shearing adapted the Barraquer design for use in the posterior chamber. With extracapsular extraction, the hooks may be implaced within the cleft of the capsule. However, during implantation the hooks are held under tension, and when released may fly up behind the iris and seat directly against the ciliary body. Alternatively, with extracapsular extraction, the hooks may intentionally be installed against the ciliar body.

A disadvantage of such an implant is that the hooks continuously exert tension on the ciliary body. An increase in the occurrence of retinal detachments has been noted amongst patients having such Shearing or Barraquer posterior chamber lenses. It is likely that the retinal detachments are associated with the tension exerted on the side of the eye in the vicinity of the ciliary sulcus. Furthermore, tenderness also is noted with such lens when the eye is rubbed.

Thus it is another object of the present invention to overcome these disadvantages by providing a posterior chamber lens in which tension is not exerted on the ciliary sulcus, but which lens nevertheless is self-centering and fixated without suturing.

A further form of posterior chamber lens was developed by Pearce. This lens generally resembles a three-bladed airplane propeller, the blades of which are inserted into the fornix of the capsule after extracapsular extraction. The disadvantage of the lens is that it is of fixed size. Thus the surgeon must take several different sizes into the operating room. If the first does not fit, he must remove this from the eye and insert another of smaller or larger size. It is also recommended to be sutured for centration. The surgical procedure itself is made unnecessarily complex. This disadvantage is overcome by the present invention, another objective of which is to provide a lens implant which will self-adjust to different eye sizes.

Still another form of prior art intraocular lens that is advantageously used with extracapsular extraction is the Binkhorst iridocapsular lens. This is a variant of Binkhorst's iris clip lens, but it does not have anterior loops. The optical portion itself is centered in the pupil with the rim of the lens lightly touching the front of the iris. The single pair of loops, bent slightly rearward, lie behind the lens and are buried in the iridocapsular cleft. After the surgery, the capsule fibroses or develops iridocapsular adhesions which embed part of the posterior loops, thereby giving extra stability to the implanted lens.

Another object of the present invention is to provide a posterior chamber lens that is also stabilized by capsular fibrosis, but in which the lens is situated entirely behind the pupil.

Another problem associated with prior art posterior chamber lenses concerns the difficulty in performing a discission. After extracapsular cataract extraction and intracocular lens implantation, it often becomes necessary to make an opening in the intact posterior capsule. This procedure is difficult when using a posterior chamber lens such as the Shearing, Barraquer or Pearce lens which has a planar rear surface that seats directly against the posterior capsule. To make the discission, the surgeon must sneak in a knife behind the lens to make the cut. This is difficult to do without knocking the lens out of place. A further object of the present invention is to provide a posterior chamber lens which facilitates the performance of a discission.

One of the reasons that a discission of the central posterior capsule may be required is to eliminate clouding due to the growth of lens fibers or of capsular fibrosis posterior capsule subsequent to extracapsular extraction. Although the capsule itself is inanimate, it is virtually impossible to clean off all of the living lens cells when the cataract extraction is performed. As time goes by, the remaining cells continue to grow and proliferate, forming the glistening, bubbly material called Elschnig's pearls. Seeing is impaired, and the discission is required to restore normal sight. In addition to facilitating such discission, a further object of the present invention is to provide a lens which itself is configured to inhibit the growth of lens fibers into the central area of the posterior capsule, so that the lens itself may reduce the incidence of impaired vision due to the growth of fibers or pearls subsequent to lens implantation.

Another potential problem associated with posterior chamber lenses is that their smooth anterior surface might, by anatomical positioning, occlude the pupil. This makes it mandatory that a peripheral iridectomy (i.e., an opening through the iris) be created to provide a fluid flow path from the posterior to the anterior chamber. This iridectomy prevents "pupillary block." It has been found that some iridectomies are incomplete, transitory or unsuccessful. With time, fluid flow may be blocked. A further object of the present invention is to provide a posterior chamber lens which itself allows for the egress of fluid and prevents pupillary block.

SUMMARY OF THE INVENTION

These and other objectives are achieved by providing a posterior chamber intraocular lens having a central optical portion, typically plano-convex, from diagonally opposite edge portions of which there extend two groups of pliant hairs. The hairs advantageously are arranged in a common plane, and diverge somewhat like the rays of the sun. The loci of the free ends of the hairs is generally circular. The hairs advantageously are less than about 0.2 mm in diameter, and are intended to be inserted into the cleft or fornix of the capsule subsequently to extracapsular cataract extraction.

The resilience of the multiple hairs is sufficient to center the lens. This is aided by providing the end of each hair with a rounded or knob-like surface to allow for easy movement in the capsular equator after placement. Over a period of time, fiber growth in the capsule fornix region will bond the hairs in place, thereby fixing the position of the lens. Centration and fixation thus both are accomplished without the need for suturing. Moreover, very little tension is imposed on the peripheral support zone of the capsule by the multiple hairs. Even this little tension is reduced or eliminated by the fibrosis subsequent to implantation. Thus virtually no tension is placed on the peripheral structure or ciliary sulcus of the eye. Moreover, the flexibility of the hairs may permit a single size lens to be used regardless of eye diameter.

To facilitate discission, and possibly to prevent the encroachment of growth of lens fibers or pearls in the central posterior capsule region, the rear surface of the lens is provided with a rearwardly projecting substantially annular ridge or lip. This posterior lip seats against the front of the posterior capsule, thereby creating a free space behind the lens. At least one section of the posterior lip is missing, thereby providing an opening through which the discission instrument can be inserted into the free space behind the lens. This permits a discission to be safely and easily performed, without dislocation of the lens. The posterior lip also may limit the extent of vitreous movement in front of the posterior capsule, and prevent the contact of vitreous with anterior chamber structures subsequent to a discission.

In an alternative embodiment of the invention, the lens may contain one or more fluid flow channels leading from the rear of the lens near the periphery, to the front of the lens near the optical center. Such channels, which may be formed by laser drilling techniques, would allow fluid to flow from the posterior chamber through the lens to the pupil. The channels thus may eliminate the need for an iridectomy, and prevent pupillary block.

In still another embodiment of the invention, the front central region of this or any other style intraocular lens may be provided with one or a small number of small sharp prongs. In the event that the lens did come up against the cornea, instead of the whole lens striking the cornea, only the few projecting prongs would touch. Thus only the endothelial cells in the very small area of contact of the prongs would be destroyed. Use of the prongs thus may eliminate the problem of substantial endothelium destruction which has been known to occur as a result of large area contact between the dislodged prior art lenses and the cornea.

BRIEF DESCRIPTION OF THE DRAWINGS

A detailed description of the invention will be made with reference to the accompanying drawings, wherein like numerals designate corresponding parts in the several figures.

DESCRIPTION OF THE PREFERRED EMBODIMENTS

Figure 7:
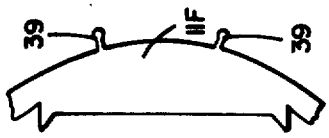
FIG. 7 shows an alternative embodiment of the invention in which the front of the lens is provided with short prongs to minimize corneal contact.

The following detailed description is of the best presently contemplated modes of carrying out the invention. This description is not to be taken in a limiting sense, but is made merely for the purpose of illustrating the general principles of the invention since the scope of the invention best is defined by the appended claims.

Operational characteristics attributed to forms of the invention first described also shall be attributed to forms later described, unless such characteristics obviously are inapplicable or unless specific exception is made.

In the embodiment of FIGS. 1 through 4, the invention posterior chamber intraocular lens 10 includes a central optical region or lens body 11 which advantageously, but not necessarily, is of plano-convex cross-section. In a manner known per se, the optical region 11 may be lathe ground or molded to provide the desired optical correction. Projecting from opposite rim portions 11a, 11b of the body 11 are two sets 12a, 12b of pliant centering hairs or filaments 12. As described in conjunction with FIG. 5 below, the filaments 12 function to center and retain the lens 10 within the capsule of the eye.

To this end, the centering hairs 12 may be arranged in a common plane (FIGS. 3 and 4) that is generally parallel to the rear surface 11R of the optical region 11. The free or distal end of 12e of each hair 12 is rounded or knob-like. The loci of these ends 12e advantageously is circular, to correspond to the equatorial shape of the eye capsule. However, the ends 12e may assume this circular loci configuration when bent slightly.

Typically, the diameter of each centering hair 12 may be on the order of 0.1 mm to 0.2 mm. The number of hairs 12 is not critical. If more hairs are used, the individual hair diameter may be reduced. Thus, many hairs 12 each having a diameter of less than 0.1 mm may be employed. Generally, the number of hairs 12 will be inversely proportional to the individual hair diameter, thereby ensuring sufficient overall resilience to achieve the requisite lens centration.

Alternatively, each hair 12 may be replaced by a small pliant loop or U-shaped filament (typified by the loop 12U in FIG. 2) made of like material and filament diameter, and also arranged so that the closed ends of the loops or U-shaped filaments define a generally circular loci.

The lens 10 advantageously is used following extracapsular cataract extraction. Thus in FIG. 5, the lens 10 is shown implanted in a human eye 13, in the posterior chamber 14 behind the iris 15. The occluded cellular material (i.e., the cataract) has been extracted from the capsule 16, leaving intact the posterior capsule 16P and an annular flap portion 16A of the anterior capsule. The capsule 16 remains connected to the ciliary muscle (in the eye wall region 17) via the suspensory ligaments or zonules 18. Vitreous humor in the region 19 behind the capsule 16 is blocked from flowing forward by the posterior capsule 16P, which assumes a generally planar shape subsequent to cataract extraction.

Typically the lens 10 is implanted through an incision around a portion (e.g., 140°) of the periphery of the cornea 20 in the region of the angle 21. The pupil 22 is dilated. The iris 15 is depressed slightly to permit one set 12a of the centering hairs 12 to be inserted into the cleft or fornix 16C of the capsule 16. For example, if the surgical incision is centered at the twelve o'clock (12:00) position, the set of hairs 12a first may be inserted into the cleft 16C at the 6:00 position. Then, the set of hairs 12b is guided into place at the 12:00 position within the capsule cleft 16C'.

Upon implantation, the resiliency of the filaments 12 will align the lens body 11 with the center of the pupil 22. The hairs 12 will assume the general arrangement shown in FIG. 2, with each end 12e in contact with the equator 16E of the capsule 16.

Within a perod of weeks after implantation, fibers 23 will grown within the capsule cleft 16C. This fibrosis will surround the hairs 12, thereby fixing the lens 10 in place. No sutures are required for such fixation. The fibrosis also will reduce to virtually zero the peripheral tension exerted by the hairs 12. As a result, there is no tenderness when the eye is rubbed, which was an adverse side effect of prior art posterior chamber lenses of the type which exerted tension on the region 24 of the ciliary sulcus. The likelihood of retinal detachment or iritis resulting from such tension also is eliminated.

The lens body 11 may be formed from a clear plastic such as polymethyl methacrylate, such as that sold commercially under the trademark PERSPEX CQ by the Imperial Chemical Industries of London, England. It may be injection molded from medical grade PMMP such as that sold commercially by Rohm and Haas. The filaments 12 may be formed individually, and inserted into fine holes 25 (FIG. 1) drilled in the periphery of the rim portions 11a, 11b. A press fit is satisfactory. The hairs 12 need not be made of the same material as the lens body 11. Thus the hairs could be formed of fine monofilament nylon such as that sold under the trademark SUPRAMID or a polypropylene such as that sold under the trademark PROLENE.

In general, the filaments 12 near the center of each set 12a, 12b are straight or approximately straight, while the filaments to either side may be curved. The overall distance between the end 12e of the filament 12 at the 6:00 position and the end of the filament at the 12:00 position may approximate the largest diameter capsule typically encountered in the human eye. The same lens 12 may be installed in an eye having a smaller capsule, by slightly bending all of the filaments 12, as illustrated generally in FIG. 6. In this way, a lens 10 of one size may be implanted in eyes having capsules 16 of different diameter.

Figure 6:
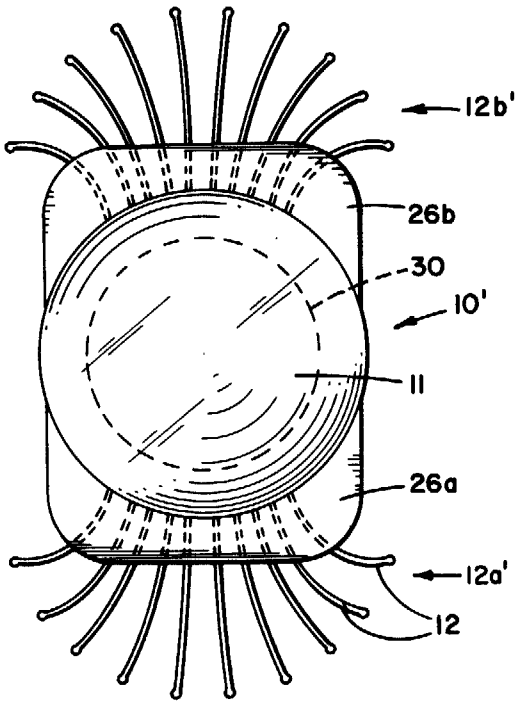
FIG. 6 is a top plan view of an alternative embodiment of the invention in which the centering hairs project from haptic portions of the lens.

In the embodiment of FIG. 6, the filaments 12a', 12b' project from a pair of haptic sections 26a, 26b. Otherwise, the lens 10' corresponds to the lens 10 of FIG. 2. In both of the lenses 10 and 10', the two sets of hairs 12 extend over opposed lens peripheral regions each of about 45°. However, the invention is not so limited, and the filaments could extend over larger or smaller peripheral regions. The sets 12a, 12b may be situated at other than the six o'clock and twelve o'clock positions, for example, at the three o'clock and nine o'clock locations. Alternatively, more than two sets of filaments could be used. For example, three such sets could be centered 120° apart around the periphery of the lens body 11.

Figure 1:
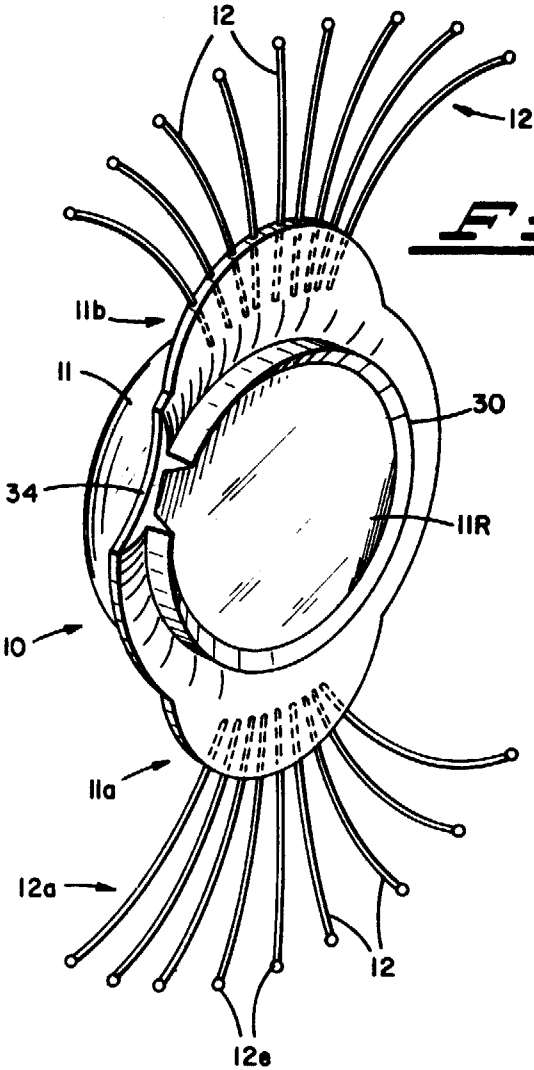
FIG. 1 is a rear perspective view of one embodiment of the inventive posterior chamber intraocular lens.
Figure 2:
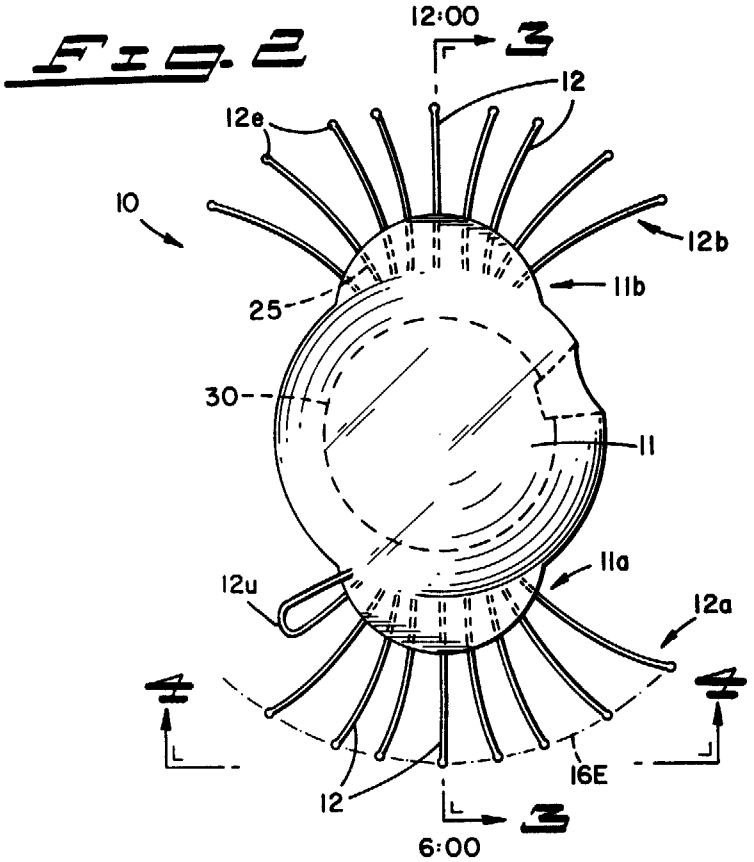
FIG. 2 is a top plan view of the lens of FIG. 1.
Figure 4:
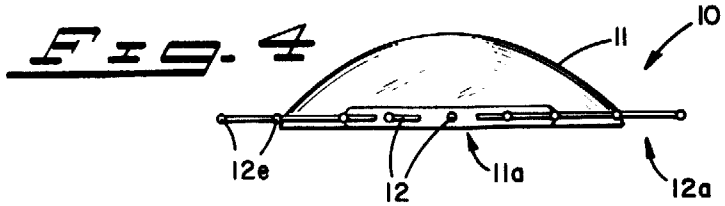
FIG. 4 is a side plan view of the lens of FIG. 1, as viewed along the line 4—4 of FIG. 2.

Another feature of the invention is the incorporation of an annular lip or ridge 30 (FIGS. 1 and 5) which projects rearwardly from the rear surface 11R of the lens body 11. As evident in FIG. 5, this lip 30 seats against the posterior capsule 16P and creates a space 31 between the capsule and the rear of the optical region 11. Advantageously, one or two sectors 34 on the nasal and/or temporal side of the lens 10 may be missing from the lip 30 (FIGS. 1 and 2). These openings 34 provide an entryway through which a knife or other instrument may be inserted into the space 31 safely to perform a discission without dislodging the lens 10.

The lip 30 also may provide a barrier for preventing vitreous from coming forward into the anterior chamber 36 (FIG. 5) after a discission has been done. The vitreous will enter the space 31 through the opening that has been made in the posterior capsule 16P. However, the lip 30 will restrict its radial flow on the forward side of the posterior capsule, and little or no vitreous will pass both the opening 34 and the lens rim 11a, 11b toward the anterior chamber.

Further, should fiber growth or pearl development begin on the forward surface of the posterior capsule 16P, outside of the lip 30, this lip may serve as a barrier to prevent such fiber development from expanding into the space 31. In this way, the lip 30 may prevent occlusion of the center of the posterior capsule 16P subsequent to lens 10 implantation.

Figure 5:
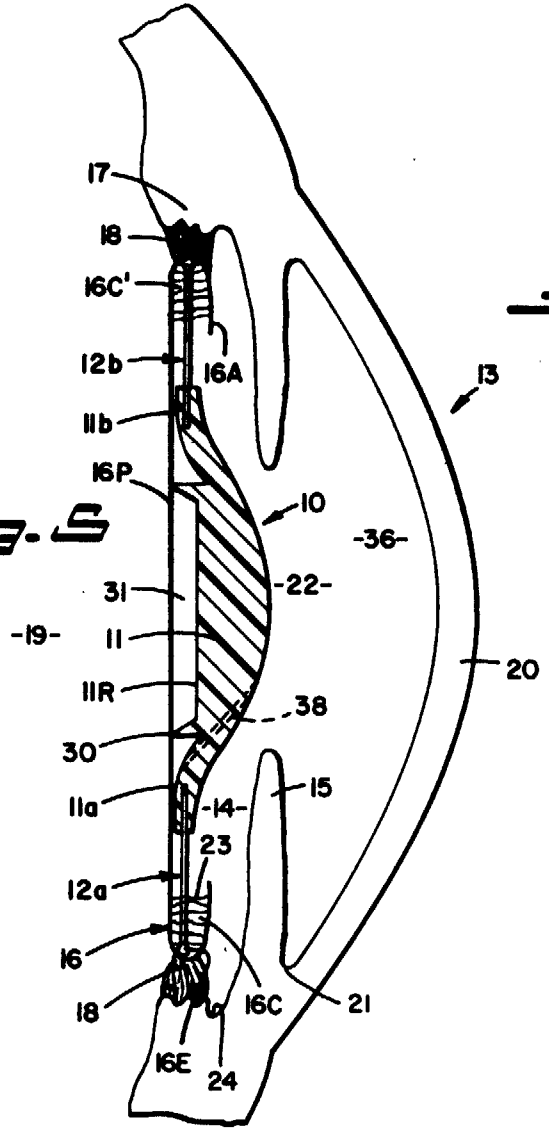
FIG. 5 is a transverse sectional view through a portion of the human eye, showing the lens of FIG. 1 implanted within the capsule following extracapsular cataract extraction.
Figure 3:
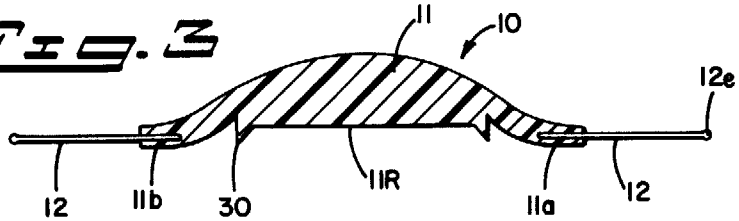
FIG. 3 is a transverse sectional view of the lens of FIG. 1 as viewed along the line 3—3 of FIG. 2.

In the embodiment shown in FIGS. 3 and 5, the rim portion 11a, 11b of the lens 10 has a rear surface situated in about the same plane as the crest of the lip 30. This provides a relatively large seating contact area for the lens 10 against the posterior capsule 16P. However, this arrangement is not necessary. The rear surface of the rim portions 11a, 11b, may be coplanar with the rear surface 11R of the lens body 11. In that event, the lip 30 may actually depress the central region of the posterior capsule 16B rearwardly.

An optional feature of the invention, intended to eliminate pupillary block, is illustrated in FIG. 5. One or more small channels 38 are provided through the lens body 11, originating at the rear of the lens, outside of the annular lip 30, and opening to the front of the lens 11 in the region of the pupil 22. These may be formed by laser drilling.

The channels 38 eliminate the following pupillary blockage problem. Normally, aqueous fluid is produced by the ciliary body near the regions 17 and 24. This fluid must go through the pupil and come up into the canal of Schlem or the trabecular meshwork and out of the eye. An iridectomy normally is performed to permit such passage. However, the iridectomy may become plugged. Further, since the lens 10 is situated behind, but relatively close to the iris, it is possible that the iris could stick down against the front surface of the lens. In that event, no fluid passageway would remain, resulting in pupillary block. The channels 38 ensure a flow path to eliminate this problem.

It is anticipated that the lens 10 will be quite light in weight, typically less than about 5 mg in aqueous. It is conceivable that the lens could become dislodged and float free into the anterior chamber. In this rare event, or if the anterior chamber should flatten, it is desirable to minimize or eliminate contact with the endothelial cells on the cornea. To this end (FIG. 7), the front surface 11F of the optical region 11 may be provided with a few small projecting prongs 39, which may be pointed. Thus if the lens did migrate forward toward the cornea, instead of the entire lens surface rubbing the cornea and causing substantial or total damage to the endothelium, only the few points of the prongs 39 would touch the cornea. Endothelial cell destruction may be limited to the region of these points.

Although the present invention has been described in terms of a posterior chamber lens intended for implantation into the capsular fornix, the invention is not so limited. It may be possible, though not preferred, to mount the lens 10 with the centering hairs seated against the region 24 of the ciliary sulcus. In this manner, the lens 10 could be used even with intracapsular cataract extraction. Similarly, it may be possible to mount the same lens 10 with the centering hairs 12 disposed within the angle 21. In the latter two cases, the tension exerted by the hairs 12 on either the ciliary sulcus 24 or the angle 21 will be considerably less than the tension exerted in these regions by the known prior art lenses described hereinabove. This is due to the fact that the filaments 12 are individually very pliable. The centering effect comes from the simultaneous but slight resilient forces of all of the filaments, exerted over a relatively large area. Moreover, if implanted in the region of the ciliary sulcus, fibrosis may also occur (similar to the growth of the fibers 23) which will lock the lens 10 in place and eliminate the radial tension. Such use, wherein the lens is mounted in other than the capsular fornix, should be done only after verification by extensive research.

I claim:

1. An intraocular lens useful for implantation in the capsule of an eye after extracapsular extraction, comprising:

a lens body, a plurality of pliant lens-centering filaments extending outwardly from edge portions of said lens body, the loci of the distal ends of said filaments being circular and having a diameter approximating that of said capsule, said filaments being insertable in the cleft of said capsule, the resilience of said filamens centering said lens body behind the pupil of said eye, and a substantially annular ridge extending rearwardly from said lens body, said ridge seating against the posterior capsule when said lens is implanted in said capsule, a section of said ridge being missing to permit the insertion of a discission instrument therethrough.

2. An intraocular lens according to claim 1 wherein said lens body is substantially plano-convex, said ridge extending from the planar face thereof.

3. An intraocular lens according to claim 1 wherein said edge portions each comprise a haptic section, said filaments extending from said haptic sections.

4. An intraocular lens according to claim 1 wherein said filaments are arranged in two groups projecting from diametrically opposed edge portions of said lens body.

5. An intraocular lens according to claim 1 wherein said filaments all are disposed in a common plane.

6. An intraocular lens accordng to claim 1 wherein each of said filaments has a rounded or knob-like free end.

7. An intraocular lens according to claim 1 having at least one fluid flow channel extending therethrough, and terminating in the central frontal region of said lens body.

8. An intraocular lens comprising:

a lens body, a plurality of pliant lens-centering filaments extending outwardly from edge portions of said lens body, and at least one small pointed prong projecting from the front surface of said lens body, said at least one prong limiting the potential contact between said lens and the cornea of an eye to the tip area of said at least one prong.

9. An intraocular lens intended for implantation within the human eye, comprising:

a body of transparent material, said body having a central optical region configured to provide requisite dioptic power, at least two spaced sets of pliant hairs projecting generally radially outwardly from spaced rim sections of said body, said hairs all being substantially coplanar, said hairs being bendable in said plane to engage a peripheral region within said eye, the resiliency of said pliant hairs centering said optical region with respect to said eye peripheral region, and an annular projecting *only* rearwardly from the central optical region of said body, said lip seating against the posterior capsule when said lens is implanted in the capsule of an eye after extracapsular cataract extraction, said lip spacing said lens from said posterior capsule.

10. An intraocular lens according to claim 9 and having at least one opening in said lip, said opening and the space behind said lens body permitting the insertion therethrough of an instrument to perform a discission without dislodging said lens.

11. An intraocular lens according to claim 9 wherein each of said pliant hairs is loop or U-shaped.

12. A posterior chamber intraocular lens intended for implantation in the capsule of an eye after extracapsular cataract extraction, comprising:

a lens body, centering means attached to said lens body for situating said lens in a central position within said capsule, and a generally annular lip projecting rearwardly from the rear face of said lens body, said lip being adapted to contact the posterior capsule and to space said rear face away therefrom, there being an opening in said lip through which a discission instrument may be inserted without dislodging said lens.

*13. A posterior chamber intraocular lens intended for implantation in the capsule of an eye after extracapsular cataract extraction, comprising:*

*a lens body,*

*centering means attached to said lens body for situating said lens in a central position within said capsule, and*

*a generally annular lip projecting only rearwardly from the rear face of said lens body, said lip being adapted to contact the posterior capsule and to space said rear face away therefrom.*

*14. A posterior chamber intraocular lens intended for implantation in the capsule of an eye after extracapsular cataract extraction, comprising:*

*a lens body, and*

*a generally annular lip projecting rearwardly from the rear face of said lens body, said lip being unitary with said lens body and adapted to contact the posterior capsule and to space said rear face away therefrom.*

*15. A posterior chamber intraocular lens intended for implantation in the capsule of an eye after extracapsular cataract extraction, comprising:*

*a lens body, and*

*a lip unitary with and projecting rearwardly from the rear face of said lens body, said lip being adapted to contact the posterior capsule and to space said rear face away therefrom.*

*16. A posterior chamber intraocular lens according to claim 15 wherein said lip extends sufficiently around the circumference of said lens body to act as a barrier to the growth of Elschnig's pearls.*

*17. A posterior chamber intraocular lens intended for implantation in the capsule of an eye after extracapsular extraction, comprising:*

*a lens body, and*

*a projecting integral with said lens body and extending rearwardly behind the rear face of said lens body, said projection being adapted to contact the posterior capsule and to space said rear face away therefrom, and*

*centering means, separate from said projection and attached to said lens body, for centering said lens within said chamber with said projection in contact with said posterior capsule.*

* * * * *